(12) United States Patent
Wu

(10) Patent No.: US 12,403,032 B2
(45) Date of Patent: Sep. 2, 2025

(54) NASAL DILATOR

(71) Applicant: Pei Yuan Wu, Hualien (TW)

(72) Inventor: Pei Yuan Wu, Hualien (TW)

( * ) Notice: Subject to any disclaimer, the term of this patent is extended or adjusted under 35 U.S.C. 154(b) by 162 days.

(21) Appl. No.: 18/484,975

(22) Filed: Oct. 11, 2023

(65) Prior Publication Data

US 2025/0120842 A1 Apr. 17, 2025

(51) Int. Cl.
*A61F 5/08* (2006.01)

(52) U.S. Cl.
CPC ..................................... *A61F 5/08* (2013.01)

(58) Field of Classification Search
CPC ...... A61F 5/08; A61F 5/56; A61M 2210/0618
See application file for complete search history.

(56) References Cited

U.S. PATENT DOCUMENTS

2019/0167464 A1* 6/2019 Lovato .................. A61F 5/08

FOREIGN PATENT DOCUMENTS

| TW | 201609071 A | 3/2016 |
| TW | I673076 B | 10/2019 |

* cited by examiner

*Primary Examiner* — Majid Jamialahmadi
(74) *Attorney, Agent, or Firm* — MUNCY, GEISSLER, OLDS & LOWE, P.C.

(57) ABSTRACT

A nasal dilator includes a connecting strip having two insertion portions on left and right sides thereof. The insertion portions each have two support portions. At least one end of each of the support portions has a support plate. An outer periphery of the support plate is provided with a soft pad that is elastically deformable to fit a user's nasal cavity.

4 Claims, 2 Drawing Sheets

NASAL DILATOR

FIELD OF THE INVENTION

The present invention relates to a nasal dilator, and more particularly to a nasal dilator used to dilate the nostrils of a human body for smooth breathing.

BACKGROUND OF THE INVENTION

A conventional nasal dilator, for example Taiwanese Publication No. 1673076 titled "NASAL CAVITY INSERT", includes two tubular inserts and a connecting strip connected between the two tubular inserts. The tubular insert has a guide opening toward the outside of the nostril. The guide opening is formed with air holes. A plurality of guide holes are formed on the periphery of the tubular insert. The nasal dilator is used for dilating the user's nostrils. However, the tubular insert of this nasal dilator has a fixed diameter and cannot be adjusted to fit the nostril shapes of different users. Wearing this nasal dilator will cause pain in the nasal cavity. In addition, the tubular structure of the tubular insert has a relatively large cross-sectional area, so the nasal dilator is noticeable on the user's face, which makes the user uncomfortable to go out and use the nasal dilator.

Another conventional nasal dilator, for example Taiwanese Publication No. 201609071 titled "NASAL DILATING INSERT", includes two curved inserts and a connecting strip connected between the two inserts. The end edge of the insert is provided with a support plate. The two inserts may be applied with a force to adjust the degree of curvature to match the shape of the nostrils, thereby providing the function of dilating the nostrils. However, the insert of this nasal expander has a large cross-sectional area because of its curved shape to form a ring-like structure. The nasal dilator is noticeable on the user's face, which makes the user uncomfortable to go out and use the nasal dilator. In addition, when the curvature of the insert is adjusted, the entire curved section will expand elastically. It is not possible to adjust the expansion locally. This may cause localized pain in the user's nasal cavity (Because the shape of the nasal cavity varies from person to person, the location of the pain is also different. If the insert cannot be adjusted with localized adjustment, it will make the user feel localized pain). The problem of localized pain is exacerbated by the fact that the support plate has no additional auxiliary element to match the irregular undulation of the user's nasal cavity.

In view of the above, how to improve the above problem is the primary issue to be addressed by the present invention.

SUMMARY OF THE INVENTION

The primary object of the present invention is to provide a nasal dilator, comprising a connecting strip having two insertion portions on left and right sides thereof. The insertion portions each have two support portions. At least one end of each of the support portions has a support plate. An outer periphery of the support plate is provided with a soft pad that is elastically deformable to fit a user's nasal cavity. The two support portions are connected by an upright strip. The upright strip is connected to the connecting strip. Each of upper and lower ends of the upright strip is provided with a curved strip extending sideways. One end of the curved strip is provided with a support plate facing the user's nostrils. The soft pad is extended and fitted on an outer periphery of the support portion.

In one embodiment of the present invention, the connecting strip and the insertion portions are made of high-strength materials (such as metal, carbon fiber, etc.) and have better structural strength. The upright strip and the curved strip each have a cross-sectional area less than that of the connecting strip, so that the curved strip is easier to adjust the degree of bending by exerting force than the connecting strip, while the connecting strip keeps the structural strength.

In one embodiment of the present invention, the support plate has at least one positioning hole for connecting and retaining the soft pad, and the soft pad is formed of liquid silicone and is fixed to the support plate.

In one embodiment of the present invention, the soft pad has an elastic section extending outwardly from one end of the support plate for elastic deformation corresponding to the user's nasal cavity.

In one embodiment of the present invention, the connecting strip is colored by anodizing process. In particular, the appearance of the connecting strip is colored to have a human skin color, thereby creating a hidden effect. The user does not have to worry about the noticeable appearance when he/she wears the nasal dilator.

Embodiments of the present invention will now be described, by way of example only, with reference to the accompanying drawings.

DETAILED DESCRIPTION OF THE PREFERRED EMBODIMENTS

Figure 1:
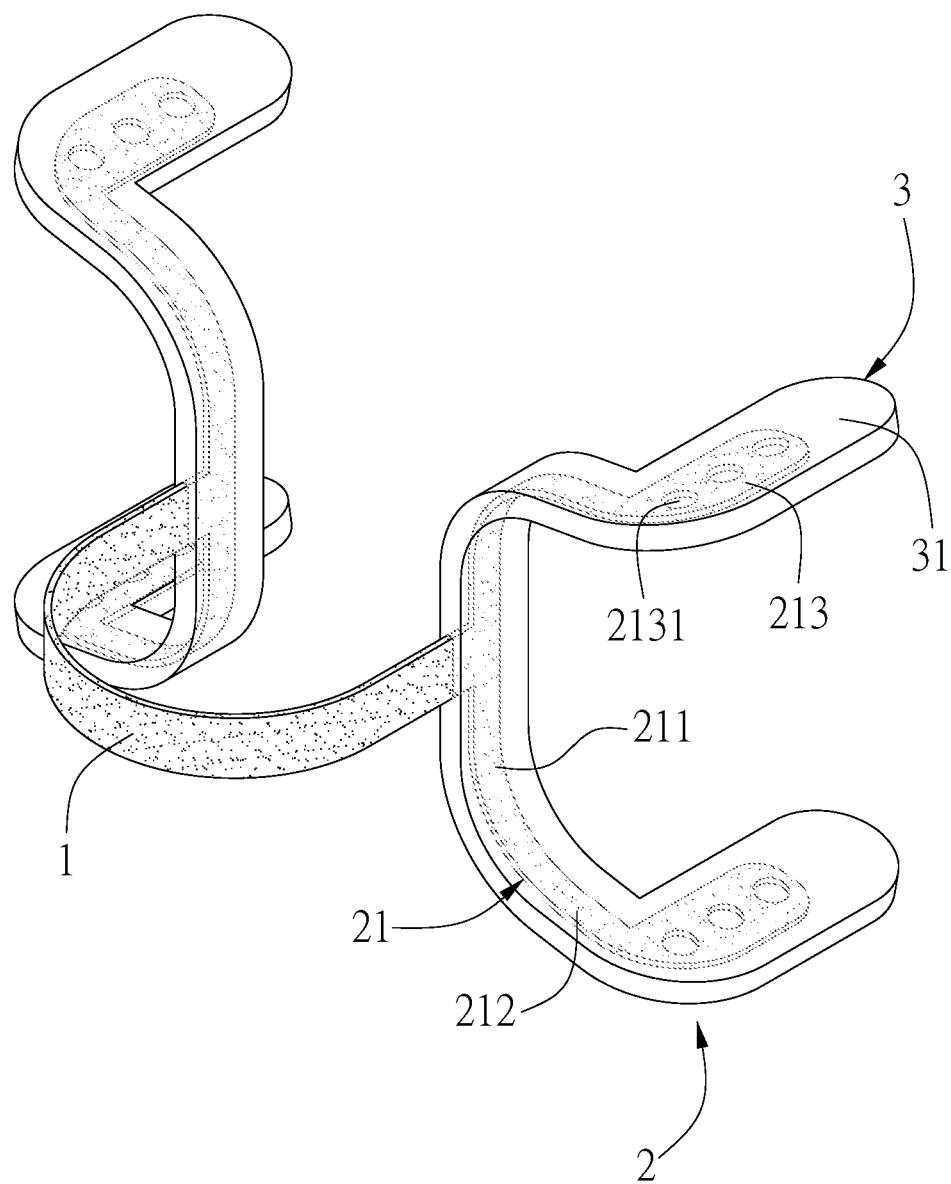
FIG. 1 is a perspective view of the present invention.

Referring to FIG. 1, the present invention discloses a nasal dilator, comprising a connecting strip 1 (it may be curved or in other shapes), and two insertion portions 2 on left and right sides of the connecting strip 1. The insertion portion 2 has two support portions 21. The two support portions 21 are connected by an upright strip 211. The upright strip 211 is connected to the connecting strip 1. Each of the upper and lower ends of the upright strip 211 is provided with a curved strip 212 extending sideways, so that the upright strip 211 and the curved strips 212 are formed into a U shape as a whole. The end of the curved strip 212 is provided with a support plate 213 facing the nostrils. The connecting strip 1 and the insertion portions 2 are made of high-strength materials (such as metal, carbon fiber, etc.) and have better structural strength. The upright strip 211 and the curved strip 212 each have a cross-sectional area less than that of the connecting strip 1, so that the curved strip 212 is easier to adjust the degree of bending by exerting force than the connecting strip 1, while the connecting strip 1 keeps the structural strength.

The support portion 21 is provided with flat support plates 213 on both upper and lower ends thereof. The outer periphery of the support plate 213 is provided with a soft pad 3 that can be elastically deformed to fit the nasal cavity. The soft pad 3 is extended and fitted on the outer periphery of the support portion 21 so that the entire insertion portion 2 is in soft contact with the nasal cavity. The support plate 213 has three positioning holes 2131 for connecting and retaining the soft pad 3. The soft pad 3 is formed of liquid silicone and is fixed to the support plate 213 through the positioning holes 2131. The soft pad 3 has an elastic section 31 extending outwardly from the end of the support plate 213 for elastic deformation according to the nasal cavity.

The connecting strip 1 is colored by anodizing process. (It may be laser colored or laser engraved to form colors, textures, and text.) In particular, the appearance of the connecting strip 1 is colored to have a human skin color, thereby creating a hidden effect. The user does not have to worry about the noticeable appearance when he/she wears the nasal dilator.

Figure 2:
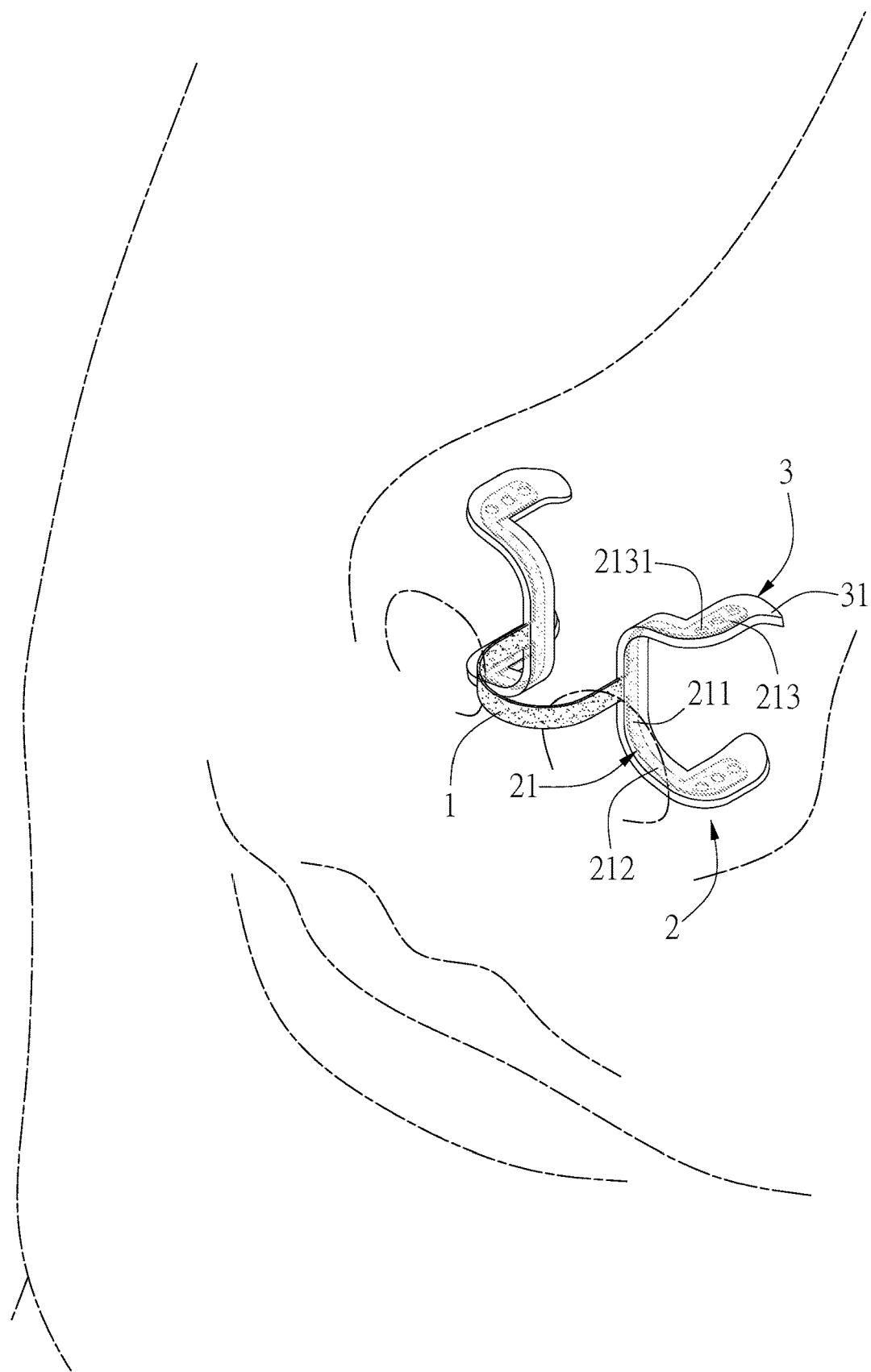
FIG. 2 is a schematic view of the present invention in a wear state.

The present invention has the following advantages (referring to FIG. 2):

1. The insertion portion 2 only has two support portions 21 extending up and down respectively. After the insertion portion 2 is inserted into the nasal cavity, it will be hidden in the nasal cavity (close to the nasal septum). Only the connecting strip 1 is exposed outside the nostril, having a very good hiding effect. The user can wear the nasal dilator, without any noticeable appearance. If the connecting strip 1 is colored with the color of human skin, the hiding effect will be more obvious.
2. The outer periphery of the support portion 21 is fitted with the soft pad 3 to be in soft contact with the nasal cavity. Particularly, the soft pad 3 has the elastic section 31 extending outwardly from the end of the support plate 213. In addition to soft contact with the nasal cavity, the elastic section 31 conforms to the undulating nasal meatus to provide a more soothing contact with the nasal cavity due to the irregularly undulating nasal meatus.
3. The cross-sectional area of the upright strip 211 and the curved strip 212 is less than that of the connecting strip 1, so the connecting strip 1 can keep the structural strength, and the curved strip 212 is easier to be bent by exerting force. The user slightly pulls the curved strip 212 to deform the curved strip 212, allowing the support portion 21 to contact the nasal cavity roughly. The soft pad 3 (as well as the elastic section 31) contacts the nasal cavity softly, so it is very comfortable for the user to wear the nasal dilator.
4. The connecting strip 1 and the insertion portion 2 are made of high-strength materials, meeting the requirements for better structural strength. The soft pad 3 is formed of liquid silicone and is fixed to the support plate 213 through the positioning holes 2131. Therefore, the soft pad 3 is coupled to the support plate 213 firmly, and the soft pad 3 formed of silicone is relatively soft and does not hurt the nasal cavity.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A nasal dilator, comprising:
a connecting strip, having two insertion portions on left and right sides thereof;
the insertion portions each having two support portions, at least one end of each of the support portions having a support plate;
an outer periphery of each of the support plates being provided with a soft pad that is elastically deformable to fit a user's nasal cavity;
the two support portions of each of the insertion portions being connected by an upright strip, each of the upright strips being connected to the connecting strip, each of upper and lower ends of each of the upright strips being provided with a curved strip extending sideways, one end of each of the curved strips being provided with a support plate of the plurality of support plates facing the user's nostrils;
each of the support plates having at least one positioning hole for connecting and retaining the soft pad, the soft pad being extended and fitted on an outer periphery of each of the support portions;
the upright strips and the curved strips each having a cross-sectional area less than that of the connecting strip;
the soft pad having an elastic section extending outwardly from one end of each of the support plates for elastic deformation corresponding to the user's nasal cavity.

2. The nasal dilator as claimed in claim 1, wherein the soft pad is formed of liquid silicone and is fixed to the support plates.

3. The nasal dilator as claimed in claim 1, wherein the connecting strip is colored by anodizing process.

4. The nasal dilator as claimed in claim 1, wherein the connecting strip is colored to have a human skin color.

* * * * *